United States Patent
Bajwa et al.

(10) Patent No.: US 12,272,455 B2
(45) Date of Patent: Apr. 8, 2025

(54) CONNECTED DEVICE FOR MEDICAL DEVICE TRANSMISSIONS

(71) Applicant: CardioAssure, Inc., Woodside, CA (US)

(72) Inventors: Husnain Bajwa, Austin, TX (US); Saqib Jang, Woodside, CA (US)

(73) Assignee: CARDIOASSURE, INC., Woodside, CA (US)

( * ) Notice: Subject to any disclaimer, the term of this patent is extended or adjusted under 35 U.S.C. 154(b) by 453 days.

(21) Appl. No.: 17/673,650

(22) Filed: Feb. 16, 2022

(65) Prior Publication Data

US 2022/0262508 A1 Aug. 18, 2022

Related U.S. Application Data

(60) Provisional application No. 63/200,153, filed on Feb. 17, 2021.

(51) Int. Cl.

| | |
|---|---|
| *G16H 40/67* | (2018.01) |
| *A61N 1/372* | (2006.01) |
| *G06N 20/00* | (2019.01) |
| *G16H 10/60* | (2018.01) |
| *G16H 40/63* | (2018.01) |

(52) U.S. Cl.
CPC ......... *G16H 40/67* (2018.01); *A61N 1/37282* (2013.01); *G06N 20/00* (2019.01); *G16H 10/60* (2018.01); *G16H 40/63* (2018.01)

(58) Field of Classification Search
CPC ........ G16H 40/67; G16H 10/60; G16H 40/63; G06N 20/00
See application file for complete search history.

(56) References Cited

U.S. PATENT DOCUMENTS

| | | | |
|---|---|---|---|
| 9,877,332 B1* | 1/2018 | Bonn | H04W 72/56 |
| 2006/0017576 A1* | 1/2006 | Gordon | A61B 5/746 |
| | | | 600/300 |
| 2020/0126677 A1* | 4/2020 | Meglic | G16H 80/00 |
| 2021/0045640 A1 | 2/2021 | Poltorak | |
| 2021/0046234 A1* | 2/2021 | Zilbershlag | A61M 60/873 |

(Continued)

OTHER PUBLICATIONS

Annapureddy, A. et al., "Association Between Industry Payments to Physicians and Device Selection in ICD Implantation," JAMA, vol. 324, No. 17, Nov. 3, 2020, 10 pages.

(Continued)

*Primary Examiner* — Siming Liu
(74) *Attorney, Agent, or Firm* — Alleman Hall & Tuttle LLP

(57) ABSTRACT

A connected device is provided. The connected device comprises processing circuitry configured to determine that a wireless transmission originated from a medical device by inspecting the wireless transmission to identify a signal characteristic, header data, or payload data of the wireless transmission, and determining that the signal characteristic, header data, and/or payload data of the wireless transmission matches a predetermined medical device signal characteristic, header data, and/or payload data. The processing circuitry is further configured to, upon determining that the wireless transmission originated from a medical device, perform medical device-specific processing on the wireless transmission.

19 Claims, 10 Drawing Sheets

(56) References Cited

U.S. PATENT DOCUMENTS

| | | | |
|---|---|---|---|
| 2021/0169417 A1* | 6/2021 | Burton | A61B 5/4857 |
| 2022/0219001 A1* | 7/2022 | Bardy | A61N 1/3787 |

OTHER PUBLICATIONS

Arthofer, C., "Manufacturer Independent Interface for Cardiac Rhythm Management," Master Thesis, Institute for Genomics and Bioinformatics, University of Technology Graz, Jan. 2013, 78 pages.

"BHRS Standards—Minimal Data Set Expected On Cardiac Implantable Electronic Device Identification Cards," British Heart Rhythm Society, Jan. 2018, 2 pages.

"Pacemaker, ICD, and ICM Evaluations—2019 Reimbursement Overview," Biotronik, Available Online at https://biotronik.cdn.mediamid.com/cdn_bio_doc/bio29441/47390/bio29441.pdf, Jan. 1, 2019, 12 pages.

"Webinar: Remote Monitoring," Biotronik, Available Online at https://news.biotronik.com/webinar-how-to-set-up-and-manage-a-seamless-remote-monitoring-cardiac-device-clinic-practical-user-insights/, Sep. 8, 2020, 1 page.

Dunnan, T., "COVID-19 changing the way cardiologists monitor patients," WPTV, Available Online at https://www.wptv.com/news/health/covid-19-changing-the-way-cardiologists-monitor-patients, Feb. 15, 2021, 7 pages.

Forrester Research, "Biden executive order bets big on zero trust for the future of US cybersecurity," TechRepublic, Available Online at https://www.techrepublic.com/article/biden-executive-order-bets-big-on-zero-trust-for-the-future-of-us-cybersecurity/, May 24, 2021, 13 pages.

Gordon, S., "Remote Cardiac Device Monitoring: Why Aren't You Doing This Already?," Everyday Health, Available Online at https://www.everydayhealth.com/heart-health/remote-cardiac-device-monitoring-why-arent-you-doing-this-already/, Jun. 4, 2020, 13 pages.

Hewitt, J., "iPhone 12 will stop your implantable defibrillator," Medical Xpress, Available Online at https://medicalxpress.com/news/2021-01-iphone12-implantable-defibrillator.html, Jan. 8, 2021, 3 pages.

McCormick, J. et al., "Hospitals Monitor Some Coronavirus Patients at Home," Ninety One, Available Online at https://91.life/news/hospitals-monitor-some-coronavirus-patients-at-home/, Apr. 15, 2020, 3 pages.

Lou, N., "Arrhythmia Clinics: Device Settings Can Make Data Dumps More Manageable," Med Page Today, Available Online at https://www.medpagetoday.com/cardiology/arrhythmias/90918?kid=nl_mpt_DHE_2021-01-28&eun=g1149398d0r&utm_source=Sailthru&utm_medium%E2%80%A6, Jan. 27, 2021, 3 pages.

McCarthy, M., "Medtronic partners with cybersecurity startup Sternum to protect its pacemakers from hackers," Tech Crunch, Available Online at https://techcrunch.com/2021/04/16/medtronic-partners-with-sternum-iot-cybersecurity-startup-to-protect-its-pacemakers-from-hackers/, Apr. 16, 2021, 10 pages.

Mond, H. et al., "The 11th World Survey of Cardiac Pacing and Implantable Cardioverter-Defibrillators: Calendar Year 2009—A World Society of Arrhythmia's Project," Pacing and Clinical Electrophysiology, vol. 34, No. 8, Aug. 2011, 15 pages.

Tshuva, N., "If it's Not Exploitable, it's Not a Vulnerability," Sternum, Available Online at https://www.sternumiot.com/blog-posts/if-its-not-exploitable-its-not-a-vulnerability, Apr. 16, 2021, 5 pages.

Salemi, T., "Medtronic's Kowal explains how remote medtech got its groove back," Mass Device, Available Online at https://www.massdevice.com/is-remote-medtech-entering-a-renaissance/, Jan. 8, 2021, 11 pages.

"Seeking Excellence in Cardiac Device Management—Pathways to Continuous Improvement," Murj, Available Online at https://murj.com/seeking-excellence-in-cardiac-device-management/, Oct. 8, 2020, 34 pages.

Marshall, D. et al., "Trends in Industry Payments to Physicians in the United States From 2014 to 2018," JAMA, vol. 324, No. 17, Nov. 3, 2020, 4 pages.

Brodwin, E., "Remote monitoring is rapidly growing—and a new class of patient-consumer is driving the shift," STAT, Available Online at https://www.statnews.com/technology-future-health-care/, Sep. 16, 2020, 36-48 pages.

"Strengthening Cybersecurity Practices Associated with Servicing of Medical Devices: Challenges and Opportunities," U.S. Food & Drug Administration, Available Online at https://www.fda.gov/media/150144/download, Jun. 2021, 6 pages.

Clarke, J. et al., "Remote interrogation and reprogramming for cardiac implantable electrical devices," Heart Rhythm, vol. 20, No. 4, Jan. 25, 2023, 2 pages.

Ploux, S. et al., "Remote interrogation and reprogramming of cardiac implantable electronic devices using a custom multivendor solution," Heart Rhythm, vol. 20, No. 4, Dec. 13, 2022, 5 pages.

Ferrick, A. et al., "2023 HRS/EHRA/APHRS/LAHRS expert consensus statement on practical management of the remote device clinic," Heart Rhythm, vol. 0, No. 0, May 19, 2023, 53 pages.

Baranchuk, A. et al., "Cybersecurity for Cardiac Implantable Electronic Devices," Journal of the American College of Cardiology, vol. 71, No. 11, Mar. 20, 2018, 5 pages.

Beyerbach, D., "Pacemakers and Implantable Cardioverter-Defibrillators," Medscape.com, Available Online at https://emedicine.medscape.com/article/162245-overview#a1, Oct. 11, 2019, 4 pages.

"Biotronik Home Monitoring: Information for Patients and Their Relatives," Biotronik, Available Online at https://biotronik.cdn.mediamid.com/cdn_bio_doc/bio24814/20971/bio24814.pdf, Available as Early as Jul. 5, 2022, 15 pages.

"Biotronik Home Monitoring: Patient Information," Biotronik, Available Online at https://biotronik.cdn.mediamid.com/cdn_bio_doc/bio28825/42305/bio28825.pdf, Available as Early as Oct. 1, 2020, 32 pages.

Böhm, M. et al., "Fluid status telemedicine alerts for heart failure: a randomized controlled trial," European Heart Journal, vol. 37, No. 41, Nov. 1, 2016, 10 pages.

Braunschweig, F. et al., "Remote monitoring of implantable cardioverter-defibrillators and resynchronization devices to improve patient outcomes: dead end or way ahead?", EP Europace, vol. 21, No. 6, Mar. 21, 2019, 10 pages.

Kapoor, A. et al., "Cardiac devices and cyber attacks: How far are they real? How to overcome?", Indian Heart Journal, vol. 71, No. 6, Nov. 2019, 4 pages.

"CardioMessenger Smart Technical Manual," Biotronik, Available Online at http://biotronik.cdn.mediamid.com/cdn_bio_doc/bio33518/107065/bio33518.pdf, Available as Early as Oct. 1, 2020, chapters 1-5 (pp. 4-24).

Chokesuwattanaskul, R. et al., "Data Transmission Delay in Medtronic Reveal LINQ TM Implantable Cardiac Monitor: Clinical Experience in 520 Patients," Journal of Biomedical Science and Engineering, vol. 12, No. 8, Jan. 2019, 10 pages.

Chudow, J. et al., "Comparison of Machine Learning Algorithms for Identification of Implantable Cardiac Devices on Chest Radiology, "Journal of the American College of Cardiology, vol. 75, No. 11, Mar. 24, 2020, 1 page.

Chudow, J. et al., "A Head-to Head Comparison of Machine Learning Algorithms for Identification of Implanted Cardiac Devices," The American Journal of Cardiology, vol. 144, No. 82, Dec. 28, 2020, 6 pages.

Daley, C. et al., "Data Integration and Interoperability for Patient-Centered Remote Monitoring of Cardiovascular Implantable Electronic Devices," Bioengineering, vol. 6, No. 1, Mar. 17, 2019, 10 pages.

Das, S. et al., "Cybersecurity: The need for data and patient safety with cardiac implantable electronic devices," Heart Rhythm, vol. 18, No. 3, Mar. 2021, 9 pages.

Elrod, J., "Software-as-a-Service CIED Management: Embracing the Future at the Heart & Vascular Institute of Prisma Health-Upstate," EP Lab Digest, Available Online at https://www.hmpgloballearningnetwork.com/site/eplab/software-service-cied-management-embracing-future-heart-vascular-institute-prisma-health-upstate, Oct. 2019, 4 pages.

(56) References Cited

OTHER PUBLICATIONS

Halperin, D., "Pacemakers and Implantable Cardiac Defibrillators: Software Radio Attacks and Zero-Power Defenses," Proceedings of the 2008 IEEE Symposium on Security and Privacy, Oakland, California, May 18, 2008, 15 pages.
Hayes, D. et al., "Cardiac Pacing, Defibrillation, and Resynchronization: A Clinical Approach, Third Edition," Wiley-Blackwell, Feb. 4, 2013, chapter 10 (pp. 427-553) and chapter 13 (pp. 613-651).
"HRS2020Science: New Data Demonstrate Effectiveness of App-Based Remote Monitoring of Medtronic Cardiac Devices, Significant Reduction in Complications with Micra Leadless Pacemaker," EP Lab Digest, May 8, 2020, 10 pages.
Iwai, S. et al., "Remote Device Monitoring: Be Careful What You Wish for . . . " JACC: Clinical Electrophysiology, vol. 7, No. 2, Feb. 2021, 3 pages.
Davidsson, G. et al., "Long-term Outcome of Implantable Cardioverter/ Defibrillator Lead Failure," JAMA Internal Medicine, vol. 180, No. 2, Dec. 20, 2019, 3 pages.
Krampe, N., "Medtronic App-Based System Monitors Pacemakers Remotely," Linkedin, Available Online at https://www.linkedin.com/pulse/medtronic-app-based-system-monitors-pacemakers-nathan-krampe-cfp-/?trackingId=A9zNQvHCQVa2obj4FyZDvg%253%E2%80%A6, Nov. 30, 2015, 3 pages.
Krittanawong, C. et al., "Integration of novel monitoring devices with machine learning technology for scalable cardiovascular management," Nature Reviews Cardiology, vol. 18, Feb. 2021, 17 pages.
Le, T. et al., "Assessing the Rate at Which Pacemaker and Defibrillator Patients Present to the Emergency Room with Their Manufacturer ID Card: A Cross Sectional Study," The Journal of Urgent Care Medicine, Oct. 2021, 8 pages.
Leonard, M., "Solving interoperability in healthcare with AWS Marketplace," AWS Marketplace, Available Online at https://aws.amazon.com/blogs/awsmarketplace/solving-interoperability-in-healthcare-with-aws-marketplace/, Sep. 1, 2021, 2 pages.
Lequang, J., "Scalability With Biotronik Home Monitoring®:A Case Study at a New York Electrophysiology Practice," EP Lab Digest, vol. 16, No. 6, Jun. 2016, 10 pages.
McLoughlin, P., "Understanding Patient Reluctance to the Remote Monitoring of Cardiac Implantable Electronic Devices," Journal of Nursing and Care, vol. 7, No. 3, Jul. 10, 2018, 7 pages.
Miller, C. et al., "MURJ: Building the Platform to Manage a Deluge of Data from Remotely Monitored Cardiac Devices," The MedTech Strategist, vol. 4, No. 12, Aug. 31, 2017, 3 pages.
Melman, Y. et al., "Limitations of manufacturer-recommended remote monitoring in the St. Jude Assurity/Endurity battery recall," Heart Rhythm Case Reports, vol. 7, No. 12, Dec. 1, 2021, 4 pages.
Moorman, B., "Service Models for Remote Healthcare Monitoring Systems," Biomedical Instrumentation & Technology Journal, 2010, 5 pages.
"Murj: The Cardiac Device Management Platform," The Murj Magazine, vol. 3, Available Online at https://www.fliphtml5.com/nterz/lvyr/basic, Available as Early as Mar. 29, 2021, 24 pages.
"Murj: The Cardiac Device Management Platform," The Murj Magazine vol. 2, Available Online at https://fliphtml5.com/nterz/azrp/basic, Available as Early as Mar. 29, 2021, 24 pages.
McLoughlin, G., "Digital Health Done Right: Murj," Redox, Available Online at https://www.redoxengine.com/blog/digital-health-done-right-murj/, Feb. 27, 2019, 6 pages.
"Murj Launches Murj Analytics Device Management Platform," Diagnostic and Interventional Cardiology, Available Online at https://www.dicardiology.com/product/murj-launches-murj-analytics-device-management-platform, May 17, 2019, 2 pages.
Neelankavil, J et al., "Managing Cardiovascular Implantable Electronic Devices (CIEDs) During Perioperative Care," Anesthesia Patient Safety Foundation Newsletter, vol. 28, No. 2, Available Online at https://www.apsf.org/article/managing-cardiovascular-implantable-electronic-devices-cieds-during-perioperative-care/, 2013, 15 pages.
Ngamboé, M. et al., "Risk Assessment of Cyber Attacks on Telemetry Enabled Cardiac Implantable Electronic Devices (CIED)," Computers & Security, arXiv:1904.11908vl, Cornell University, Apr. 26, 2019, 60 pages.
Ngamboé, M. et al., "Risk assessment of cyber-attacks on telemetry-enabled cardiac implantable electronic devices (CIED)," International Journal of Information Security, vol. 20, Oct. 7, 2020, 25 pages.
O'Shea, C. et al., "Remote Monitoring Alert Burden: An Analysis of Transmission in >26,000 Patients," JACC: Clinical Electrophysiology, vol. 7, No. 2, Feb. 2021, 9 pages.
Offenbaker, D., "RFID Implantation and Implementation: A Look into the Future," AllNurses.com, Available Online at https://allnurses.com/rfid-implantation-implementation-a-look-t650006/, Jun. 13, 2017, 8 pages.
Plaff, J. et al., "Chapter 13: Assessment of Implantable Devices," Roberts and Hedges' Clinical Procedures in Emergency Medicine and Acute Care, Elsevier, Feb. 21, 2018, 18 pages.
Ploux, S. et al., "Optimizing Implantable Cardioverter-Defibrillator Remote Monitoring: A Practical Guide," JACC: Clinical Electrophysiology, vol. 3, No. 4, Apr. 2017, 14 pages.
Elrod, J., "Remote Monitoring Workflow in EP: Challenges and Opportunities," EP Lab Digest, Available Online at https://www.hmpgloballearningnetwork.com/site/eplab/podcasts/remote-monitoring-workflow-ep-challenges-and-opportunities, Jan. 2, 2022, 9 pages.
Roberts, P. et al., "The Use of App-based Follow-up of Cardiac Implantable Electronic Devices," Cardiac Failure Review Journal, Apr. 9, 2020, 6 pages.
Rosman, L. et al., "Remote monitoring of implanted cardiac devices: A guide for patients and families," Pacing and Clinical Electrophysiology, vol. 41, No. 9, Sep. 2018, 6 pages.
Shams, P. et al., "Comparing sensitivity and specificity of pacemaker ID application and cardiac rhythm management device-finder application in identifying cardiac implantable electronic device manufacturer using chest radiograph—An observational study," Annals of Medicine and Surgery, vol. 69, Aug. 20, 2021, 5 pages.
Sinha, S. et al., "Managing cardiac implantable electronic device patients during a health care crisis: Practical guidance," Heart Rhythm Society, vol. 1, No. 3, Aug. 1, 2020, 5 pages.
"Telehealth and Remote Patient Monitoring for Long-Term and Post-Acute Care: A Primer and Provider Selection Guide," LearningAge.org, Available Online at https://leadingage.org/white-papers/telehealth-and-remote-patient-monitoring-long-term-and-post-acute-care-primer-and#1, Available as Early as Feb. 6, 2017, 65 pages.
Porterfield, J., "Universal Medical Device Identifier to Improve Emergency Triage," NIH RePORT Expenditures and Results, Available Online at https://reporter.nih.gov/search/RYbvJYoLdUWIP8fQlyuh4A/project-details/9977896, 2020, 4 pages.
Varma, N. et al., "Efficacy and Safety of Automatic Remote Monitoring for Implantable Cardioverter-Defibrillator Follow-Up: The Lumos-T Safely Reduces Routine Office Device Follow-Up (TRUST) Trial," Circulation, vol. 122, No. 4. Jul. 12, 2010, 8 pages.
Elrod, J., "10-Minute Interview: Nilofar H. Islam, MD, FACC, CEPS," EP Lab Digest, vol. 18, No. 1, Available Online at https://www.hmpgloballearningnetwork.com/site/eplab/feature-interview/10-minute-interview-nilofar-h-islam-md-facc-ceps, Jan. 2018, 4 pages.
Ahmed, R. et al., "Visualization of Cardiac Implantable Electronic Device Data for Older Adults Using Participatory Design," Applied Clinical Informatics, vol. 10, No. 4, Aug. 1, 2019, 14 pages.
Alexander, B. et al., "Cybersecurity and cardiac implantable electronic devices," Nature Reviews Cardiology, vol. 17, Apr. 3, 2020, 3 pages.

* cited by examiner

CONNECTED DEVICE FOR MEDICAL DEVICE TRANSMISSIONS

CROSS REFERENCE TO RELATED APPLICATIONS

The present application is based upon and claims priority under 35 U.S.C. 119(e) to U.S. Provisional Patent Application No. 63/200,153, entitled WIRELESS ACCESS POINT FOR MEDICAL DEVICE TRANSMISSIONS, filed Feb. 17, 2021, the entirety of which is hereby incorporated herein by reference for all purposes.

BACKGROUND

Some electronic medical devices collect medical data from a patient and transmit the medical data to a remote server. The medical data may be archived as part of an electronic health record (EHR), and/or accessed by a clinician, for example. In order to transmit the medical data to the remote server, the medical device is often coupled with a bedside or portable monitor that wirelessly receives the medical data from the electronic medical device and relays that medical data to the remote server by connecting to a mobile network or an intermediate network waypoint such as an ethernet router or Wi-Fi access point near the bedside or portable monitor. In addition to relaying the medical data to the remote server, the bedside or portable monitor may also process the medical data to recognize certain medical events, store the medical data in order to send it at a later time, update firmware on the electronic medical device, or perform other functions.

Despite an increase in use of these electronic medical devices, several challenges are presented with their widespread deployment. For example, conventional intermediate network waypoints cannot recognize the medical data as such and as a result may in some situations prioritize traffic of non-medical data (e.g., streaming video), over the medical data, which can lead to low transfer rates for the medical data. Electronic medical devices may send the medical data to the bedside or portable monitor when a distance between the electronic medical device and the bedside or portable monitor is great enough to require the medical data to be sent more than once, thus shortening the battery life of the medical device. This shortening of battery life is especially undesirable in the case of an implantable electronic device which may require costly and invasive surgery to replace. Because bedside or portable monitors produced by different manufacturers can utilize proprietary information formats and protocols for application-programing interface (API) integration to EHR clouds, the clinician has little flexibility in managing the medical data. Additionally, because intermediate network waypoints do not recognize the medical data, appropriate encryption or other methods of securing the medical data may not be used. Also, in an era of increased cybersecurity concerns, electronic medical devices and coupled connected medical devices, such as bedside or portable monitors, can no longer rely on layered security, such as firewalls, at intermediate network locations for protection. Adoption of zero-trust cybersecurity requires participation of an endpoint, but currently there is no effective solution that enables connected medical devices to actively participate as endpoints in such a zero-trust security architecture.

SUMMARY

To address the above issues, a connected device is provided. In one example, the connected device comprises processing circuitry configured to determine that a wireless transmission originated from a medical device by inspecting the wireless transmission to identify a signal characteristic, header data, or payload data of the wireless transmission, and determining that the signal characteristic, header data, and/or payload data of the wireless transmission matches a predetermined medical device signal characteristic, header data, and/or payload data. The processing circuitry is further configured to, upon determining that the wireless transmission originated from the medical device, perform medical device-specific processing on the wireless transmission.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

Figure 1A:
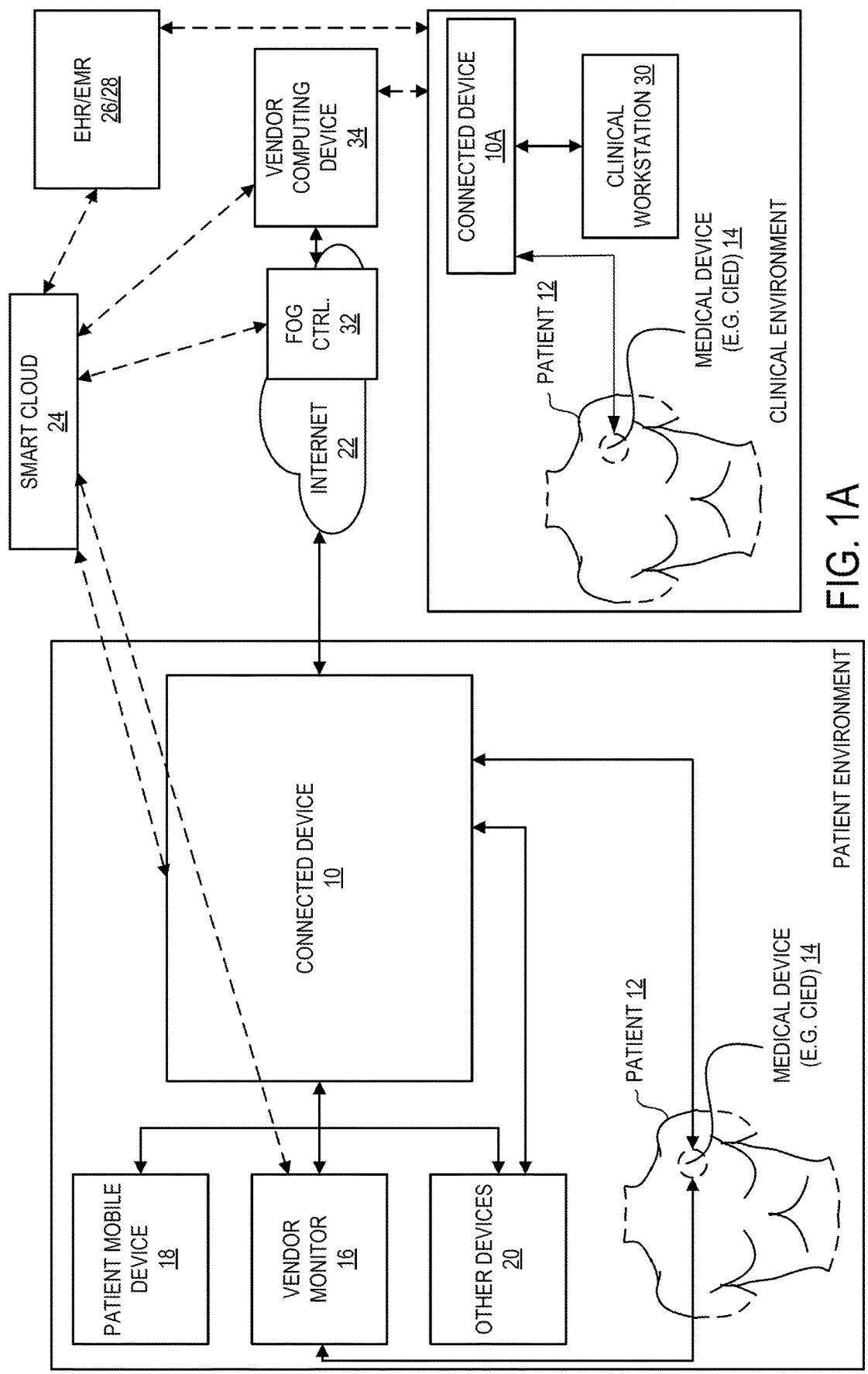
FIGS. 1A-C shows schematic views of an example environment in which a connected device may be enacted.
Figure 1B:
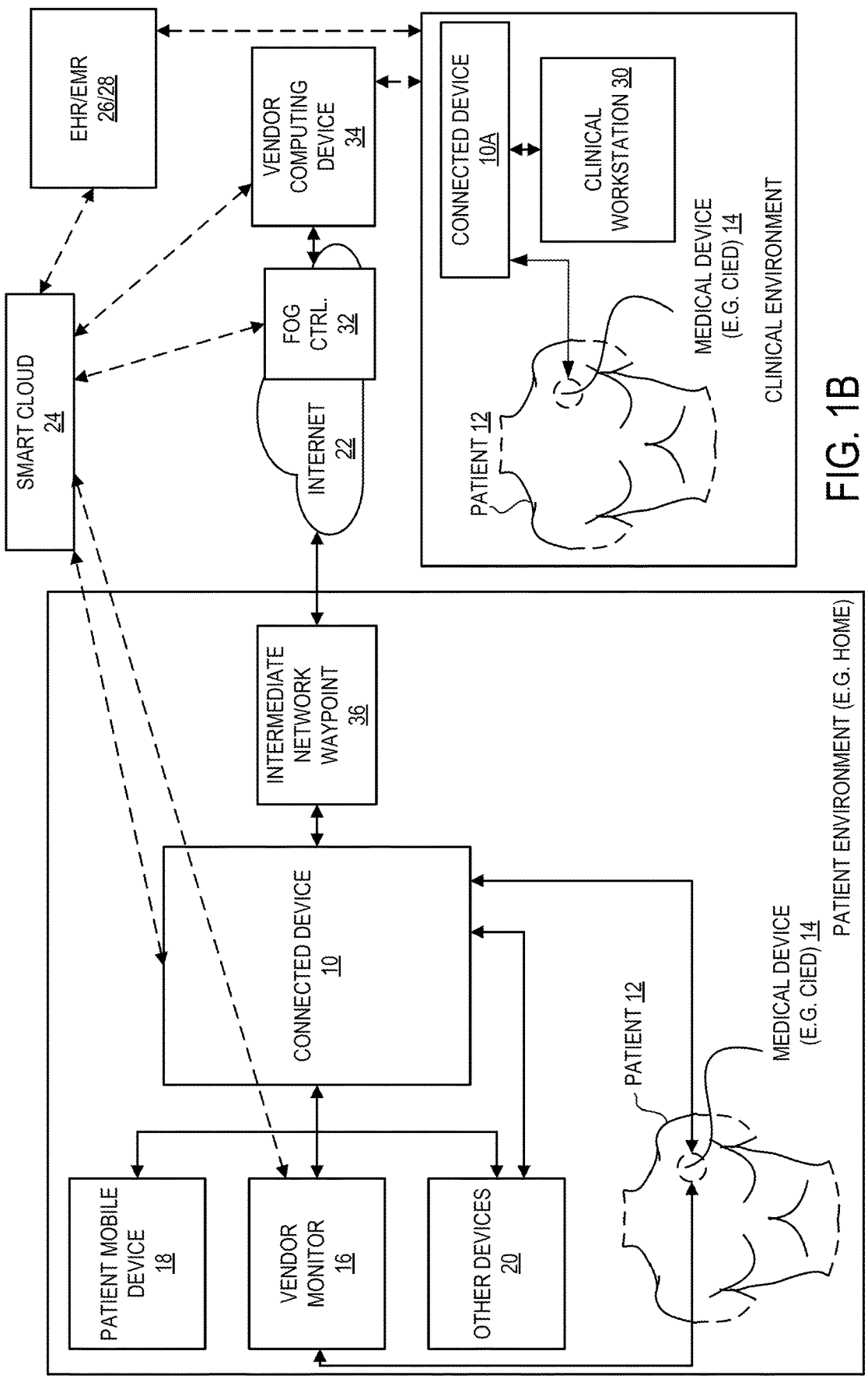

To address the above issues, FIGS. 1A-B illustrate a connected device 10 in an example target environment such as a patient environment including a patient 12 using a medical device 14. In this example, the medical device 14 is a cardiovascular implantable electronic device (CIED), however it will be appreciated that any medical device that transmits data may be used with the connected device 10. For example, the medical device 14 may be cochlear implant, a deep brain neurostimulator, a gastric electrical stimulator, a spinal stimulator, infusion pump, or other medical device. The connected device 10 is in electronic communication with the medical device 14 either directly or indirectly via a vendor monitor 16, such as a portable monitor or a bedside monitor. A portable monitor is one that can operate on battery power either primarily or as a backup power source and that can be moved during operation, whereas a bedside monitor typically operates on mains power and cannot operate when mains power is disconnected. It will be appreciated that the vendor of the vendor monitor 16 is typically a manufacturer of the medical device 14. The connected device 10 may also be in electronic communication with a patient mobile device 18 such as a mobile phone or tablet of the patient 12 and/or other devices 20 such as home computers, laptops, home security cameras, climate control systems, or smart appliances, for example. The connected device 10 is connected to the Internet 22 and configured to send medical data to a smart cloud 24 where the medical data is incorporated into electronic health records (EHRs) 26 or electronic medical records (EMRs) 28. In a clinical environment, a clinician for example, may update device settings or a firmware update, and/or to access the EHRs/EMRs 26/28 at a clinical workstation 30. As shown, the smart cloud 24 is in communication with a fog controller 32 and a vendor computing device 34. The vendor computing device 34 can be a single terminal or a server arranged in a cloud data center, as examples. The term "connected device" means a computing device that is configured to connect to a wide area network (WAN) such as the Internet 22 and to connect to a local device such as medical device 14 via a local area network (LAN), personal area network (PAN) or body area network (BAN). The WAN connection may be through a network gateway that is a separate device or integrated into the connected device.

In the example shown in FIG. 1A, the connected device 10 is configured such that it may replace intermediate network devices in the target patient or clinical environment. This installation configuration allows a high degree of control over the medical data and other data because it allows control of all data flow between the patient environment and the Internet 22 via the connected device 10. In an alternative example shown in FIG. 1B, the connected device 10 provides Wi-Fi access and is connected to an intermediate network waypoint 36 that provides router functions. To achieve this installation configuration, the connected device 10 may be connected to the intermediate network waypoint 36 while taking over Wi-Fi functions of the intermediate network waypoint 36, or by coexisting with the Wi-Fi functions of the intermediate network waypoint 36 resulting in two Wi-Fi networks in the target patient environment. Alternatively, the connected device 10 may be connected to a router not having wireless capabilities. The installation configuration depicted in FIG. 1B may be used in a scenario in which an Internet service provider (ISP) does not easily permit third party routers to be installed.

Figure 1C:
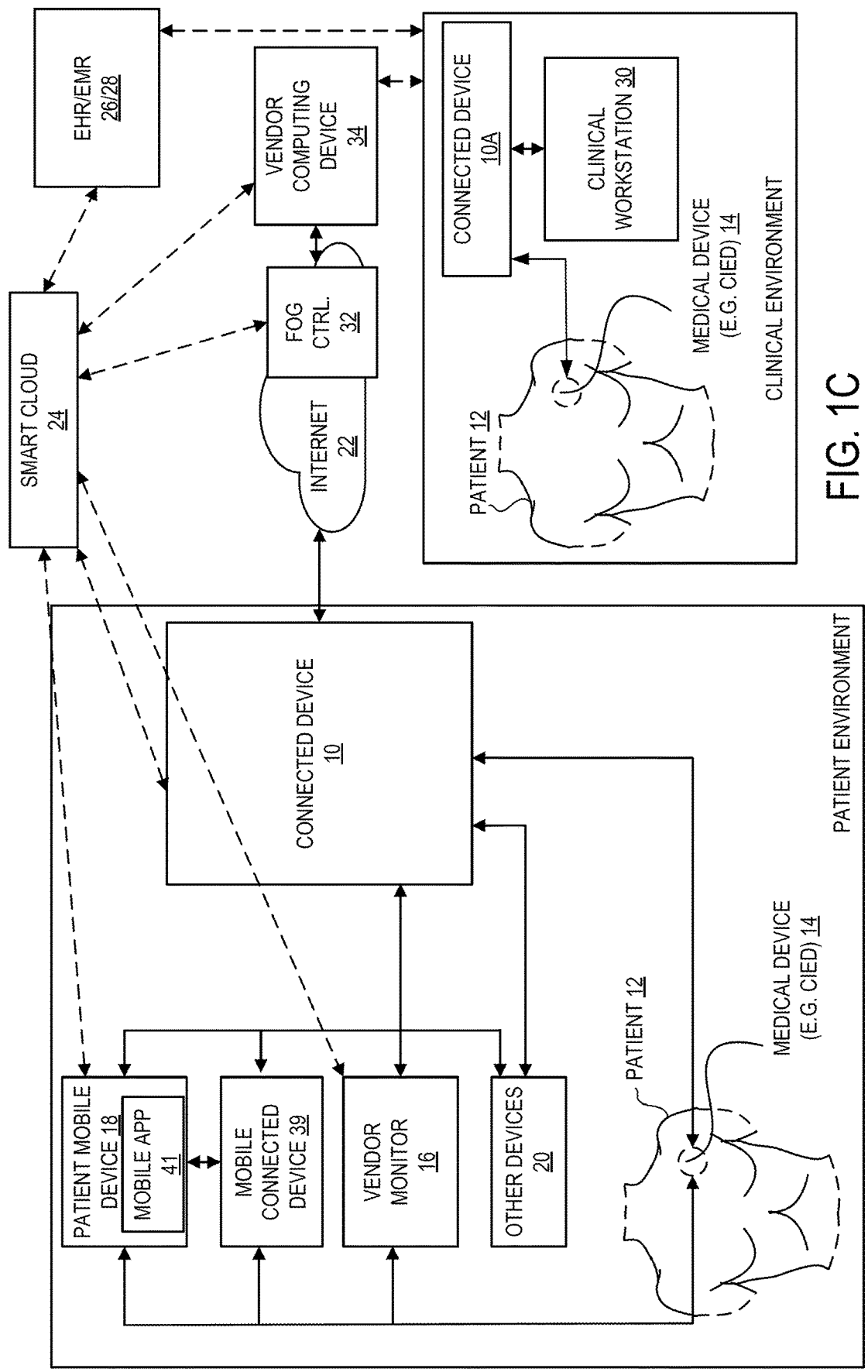

Turning now to FIG. 1C, a mobile connected device 39 is shown integrated into a target environment such as a patient environment similar to that of FIG. 1A. The mobile connected device 39 is in communication with the patient mobile device 18 via a Bluetooth radio, a headphone jack, a universal serial bus (USB) cable, or other suitable connection. The mobile connected device 39 is sized such that it is conveniently carried by the patient 12 within or outside of the patient environment. The mobile connected device 39 is configured to execute a hypervisor that is also executed by the connected device 10 and includes a MedRadio module 102, as will be discussed below. Thus, when in communication with the patient mobile device 18, the mobile connected device 39 is configured to perform the functions of the monitor 16 and the connected device 10. As shown in FIG. 1C, the mobile connected device 39 is in direct communication with the medical device 14 and communicates with the smart cloud 24 either via the connected device 10, or via the patient mobile device 18. An advantage of the mobile connected device 39 communicating via the patient mobile device 18 is that the medical device 14 maintains communication with the smart cloud 24 and the clinical environment as long as the patient mobile device 18 is able to access a mobile network. Thus, all the benefits of the connected device 10 (e.g., prioritization of medical data over other data) are available when the patient 12 leaves the patient environment. In the above described configuration, the patient mobile device 18 communicates with the smart cloud while the mobile connected device 39 performs the other functions of the connected device 10. However, the functions of the connected device 10 may be distributed between the patient mobile device 18 and the mobile connected device 39 in any way reflecting their respective hardware components. Further, in some configurations, some or all the functions of the connected device 10 can be implemented in the patient mobile device 18, without requiring the use of a mobile connected device 39.

The patient mobile device 18 is configured to execute a mobile application 41 that facilitates communication between the medical device 14, and the patient mobile device 18. This communication may occur via the connected device 10, the mobile connected device 39, and/or the monitor 16. Additionally or alternatively, the patient mobile device 18 and the medical device 14 may communicate directly via Bluetooth Low Energy (BLE), for example. The mobile application 41 includes a configuration tool that identifies the medical device 14 using the above described methods with regard to the connected device 10, or for example, by receiving a serial number or other identifier associated with the medical device 14. The mobile application 41 processes data received from the medical device 14 and includes an analytics viewer that displays the processed data. In an example scenario in which the medical device is a CIED, the analytics viewer displays, for example, a patient's heartrate over time, any abnormalities that may be detected, and a remaining battery life of the battery of the medical device 14. It will be appreciated that the analytics viewer is configured to display information based in part by the type of medical device 14 identified by the configuration tool. For example, when the medical device 14 is a gastric electrical stimulator, the analytics viewer can display a history of electrical impulses sent to a stomach of the patient 12.

It will be appreciated that the examples shown in FIGS. 1A-C are meant to illustrate alternative installation configurations of the connected device 10, and that the connected device 10 can be configured such that it may be installed in any of the above installation configurations. Furthermore, it will be appreciated that other installation configurations are possible including an installation configuration in which a plurality of connected devices 10 are installed in order to, for example, compensate for a large area requiring coverage by the connected device 10, or an area having Wi-Fi signal obstructions. In order to facilitate an installation configuration with a plurality of connected devices 10, the connected device is configured to enable wireless mesh networking. An additional advantage of deploying a plurality of connected devices in a particular environment is that a distance between the medical device 14 and any of the plurality of connected devices 10 can be reduced compared to an environment having one connected device 10. By reducing the distance between the medical device 14 and the connected device 10, a number of missed wireless transmissions from the medical device 14 may be reduced. Because sending wireless transmissions uses battery power, reducing missed wireless transmissions may extend a battery life of the medical device 14 as missed wireless transmissions are resent until they are received by the monitor 16 or the connected device 10.

Regardless of the installation configuration used, the connected device 10 functions such that it is integrated into the patient environment to optionally provide internet access to both medical devices 14 and non-medical devices while ensuring secure and efficient transmission of medical data. In order to perform these functions, the connected device 10 is configured to determine that a wireless transmission is using a licensed, lightly licensed, or unlicensed radio frequency band originated from the medical device 14. As used herein, "lightly licensed" means a frequency band where a telecommunication operator registers with the Federal Communications Commission (FCC) in order to use the frequency band and where multiple operators in the same region may share a spectrum of the frequency band. In some cases, the operator does not need to purchase a license, or in other cases, purchases or registers for a nominal fee. Examples of lightly licensed frequency bands in the United States include the 3.5 GHz band lightly licensed by the FCC. For unlicensed frequency bands, operators can operate without a license but must use certified equipment and comply with coexistence requirements, but do not have exclusive use of the spectrum in the unlicensed frequency band. Upon determining that the wireless transmission originated from the medical device 14, perform medical device-specific processing on the wireless transmission. One method by which the connected device 10 may determine that the wireless transmission including relevant line protocols originated from the medical device 14 is by inspecting the wireless transmission to identify a signal characteristic, header data, or payload data of the wireless transmission, and determining that the signal characteristic, header data, and/or payload data and underlying message encapsulation of the wireless transmission matches a predetermined medical device signal characteristic, header data, and/or payload data. One example of performing medical device-specific processing includes prioritizing processing of data contained in the wireless transmission over processing of data contained in other wireless transmissions. Prioritizing processing of data contained in the wireless transmission includes implementing quality of service (QoS) mechanisms and/or reserving a portion of bandwidth for the medical data. The portion of bandwidth being reserved may be a percentage of total bandwidth or a specific bitrate. Other examples of the medical device-specific processing are described below in the context of a software and hardware architecture.

Figure 2A:
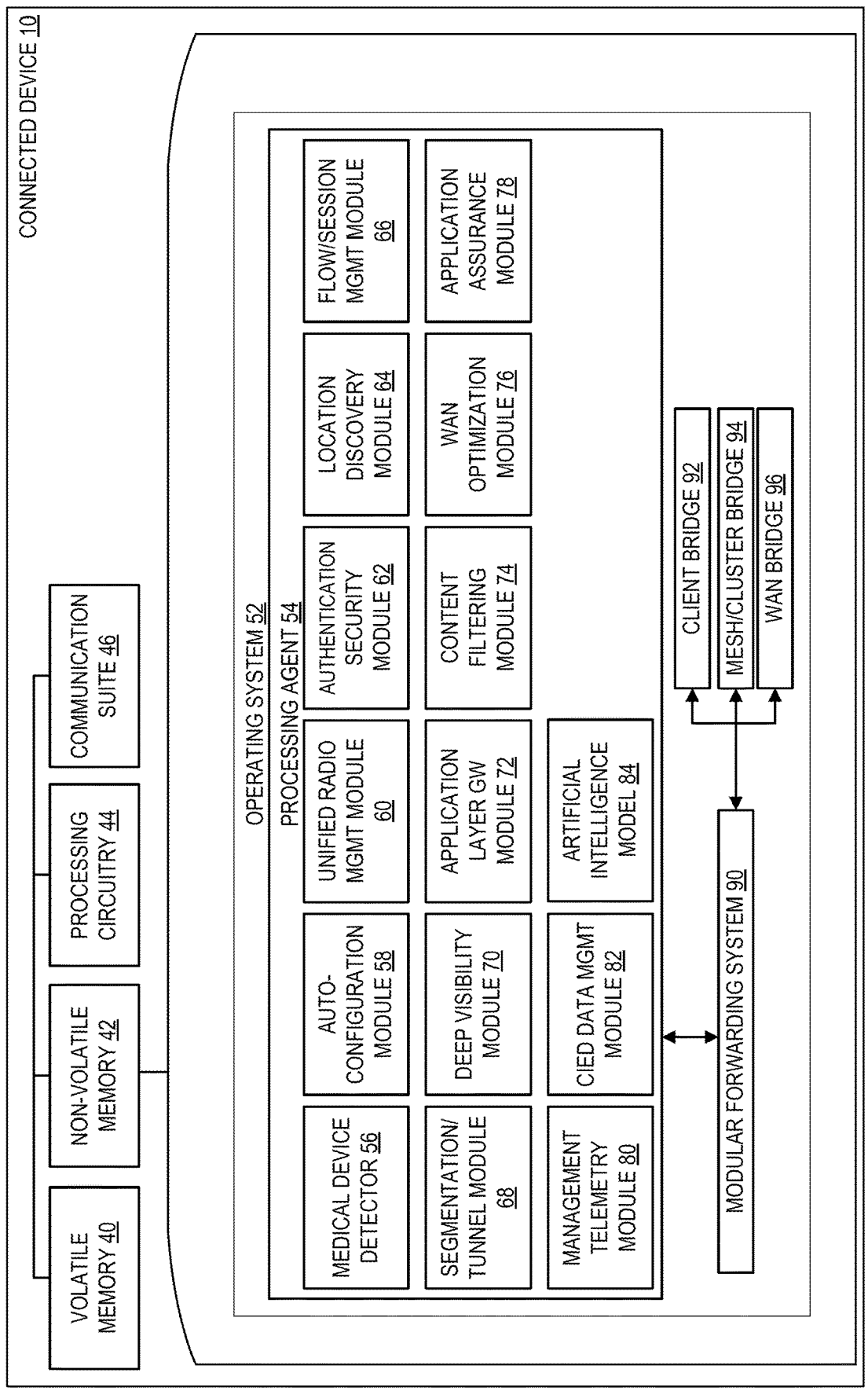
FIGS. 2A and 2B are schematic views illustrating software and hardware components of the connected device of FIGS. 1A-C.

Turning now to FIG. 2A, the software and hardware architecture of the connected device 10 is illustrated in a schematic view. The connected device 10 includes volatile memory 40, non-volatile memory 42, and processing circuitry 44. In order to communicate with a variety of medical devices 14, monitors 16, wireless networks, and other devices 20, the connected device 10 includes a communication suite 46 comprising modules (physical and virtual interfaces) for wired and/or wireless networks operating in licensed, lightly licensed, and/or unlicensed radio frequency bands that are attached to bridge components based on a configuration policy.

As discussed above, the connected device 10 is configured to determine that a wireless transmission originated from the medical device 14, and upon determining that the wireless transmission originated from the medical device 14, perform medical device-specific processing on the wireless transmission. In some examples, the connected device 10 is configured to implement a virtualized machine environment including a hypervisor communicating with one or more virtual machines in which each virtual machine includes an operating system 52 instance. In other examples, the connected device 10 is configured to implement a container environment including a container interface configured to communicate between software in one or more containers and an operating system executed by the processing circuitry 44. Each container does not include the operating system 52 instance. In yet other examples, the connected device 10 is configured to implement a serverless environment including a plurality of functional software modules that present microservice instances that process individual functions for requesting clients, such as the medical device 14. At least one instance of the virtual machine, container, or serverless instances is configured to execute a processing agent 54 including a medical device detector 56. The medical device detector 56 is configured to perform inspecting of the wireless transmission to identify the signal characteristic, header data, and/or payload data of the wireless transmission, and determining that the signal characteristic, header data, and/or payload data of the wireless transmission matches the predetermined medical device signal characteristic, header data, and/or payload data.

Figure 2B:
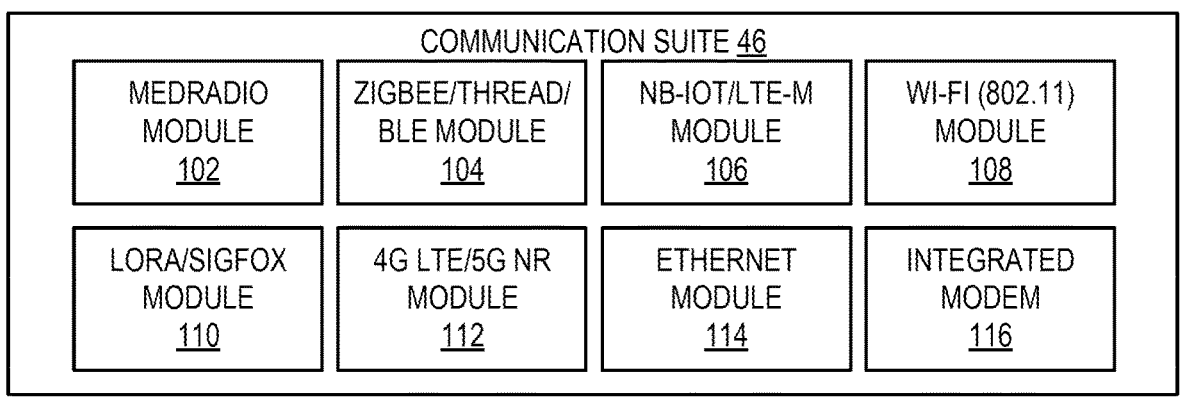
Figure 3A:
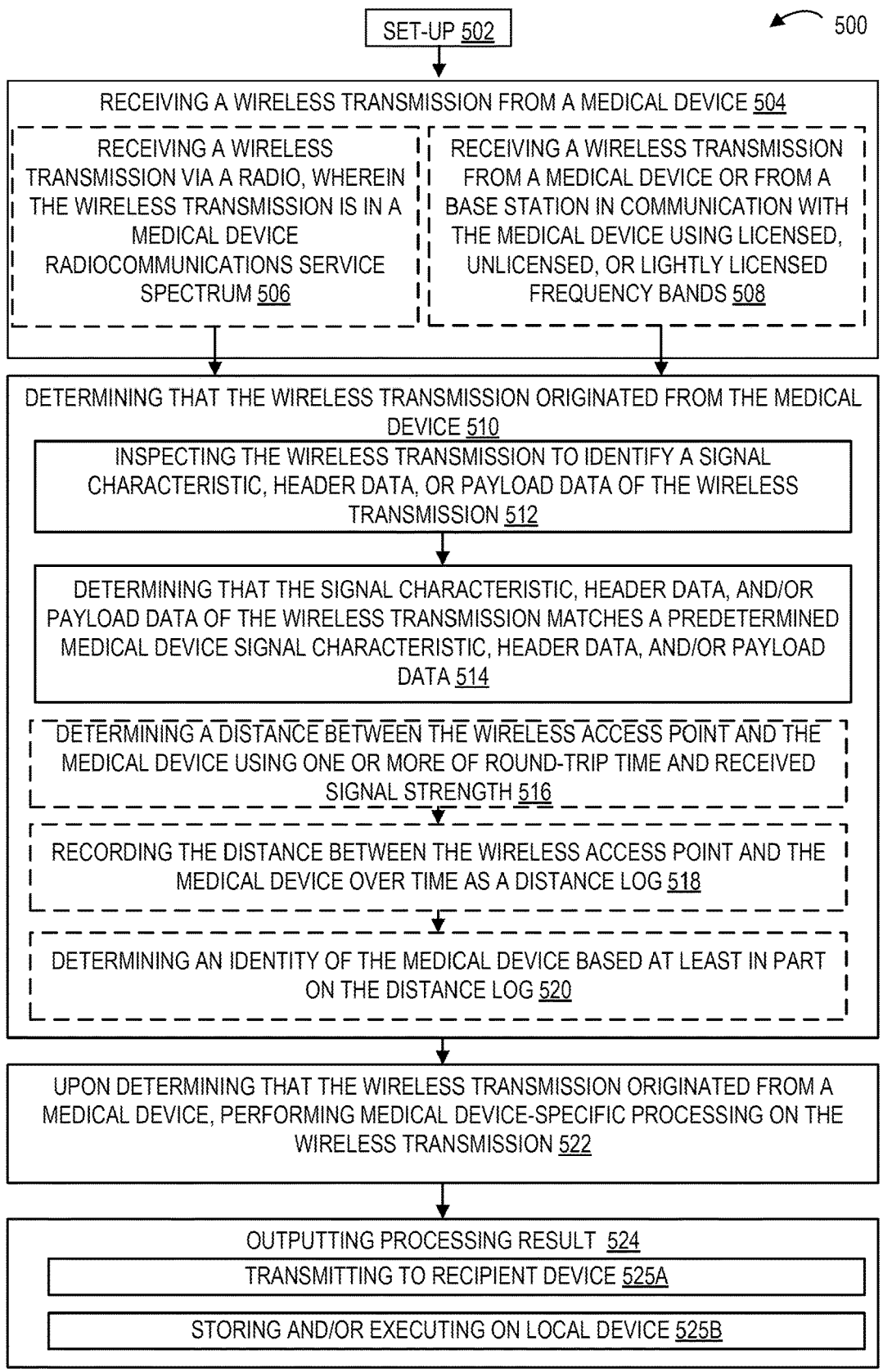
FIGS. 3A-G shows a process flow implemented by the connected device of FIGS. 2A and 2B.
Figure 3B:
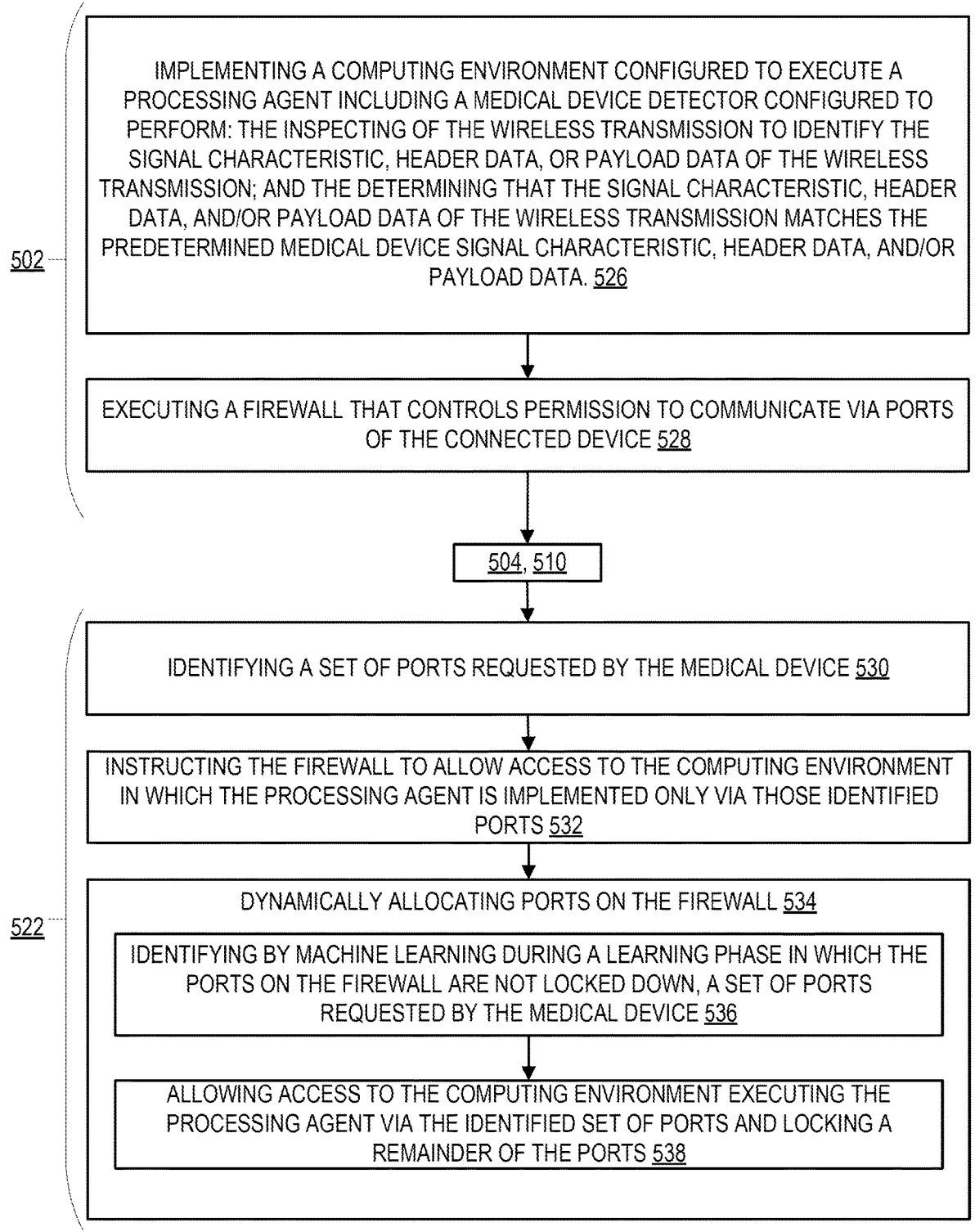
Figure 3C:
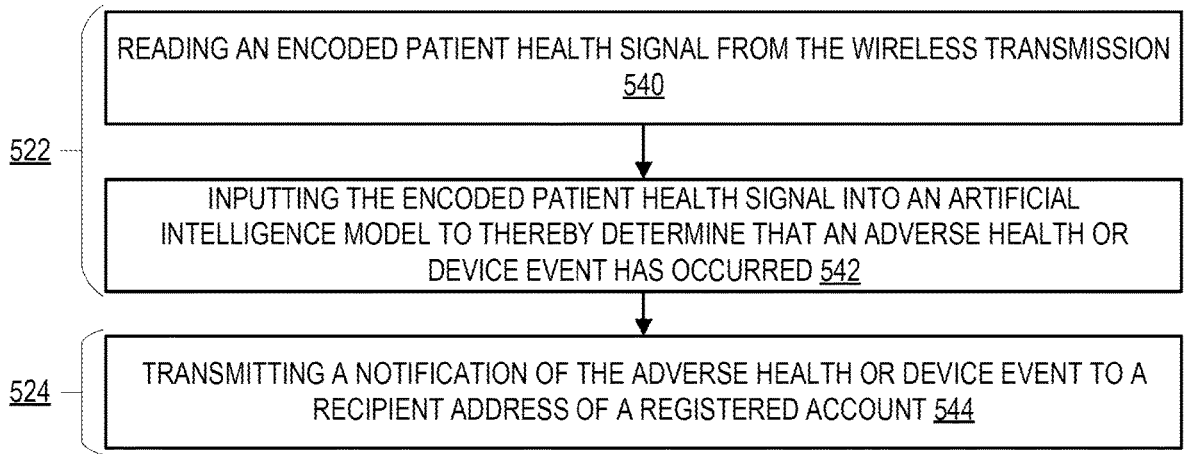
Figure 3D:
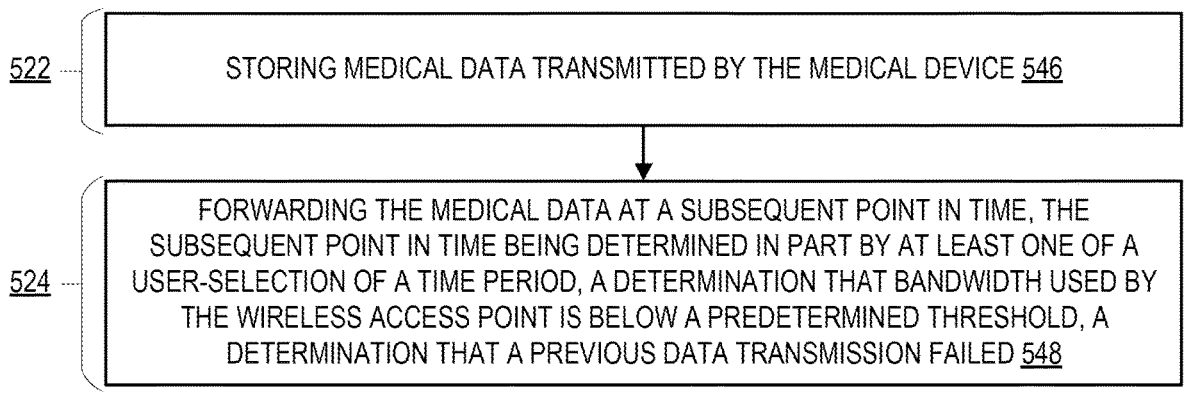
Figure 3E:
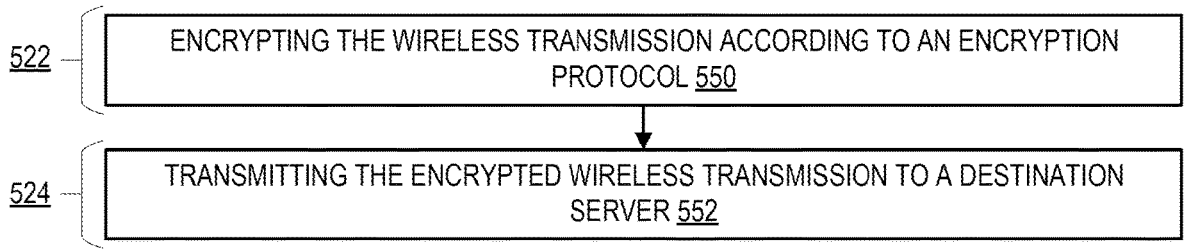
Figure 3F:
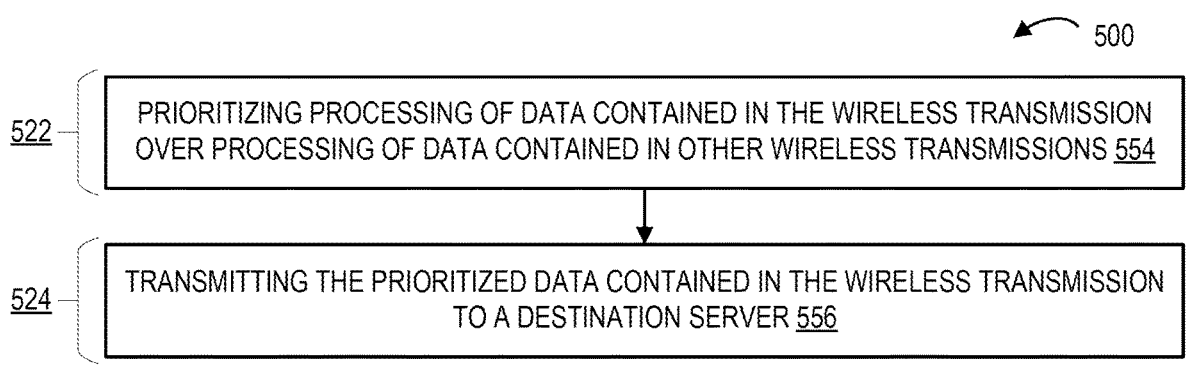
Figure 3G:
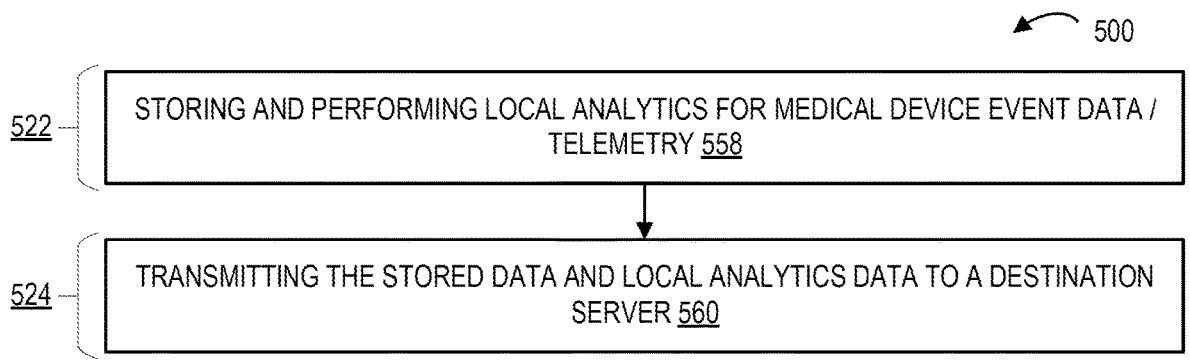

FIG. 2B illustrates the communication suite 46 in more detail. The communication suite includes a MedRadio module 102, a Zigbee module 104, a narrow-band internet of things (NB-IoT) module 106, a Wi-Fi module 108, a LoRa module 110, a long-term evolution (LTE) module 112, an ethernet module 114, and an integrated modem 116.

The MedRadio module 102 uses a radio transceiver configured to transmit and receive on the Medical Device Radiocommunications Service (MedRadio) spectrum. In a case that the medical device 14 is configured to send the wireless transmission using the MedRadio specification, the wireless transmission is received via the radio transceiver.

The Zigbee module 104 uses a radio transceiver configured to transmit and receive using the Zigbee, Thread, and/or BLE standards. These standards are often used by devices that have low power digital radios and that are used for a variety of purposes such as home automation and medical device data transmission.

The NB-IoT module 106 uses a radio transceiver configured to transmit and receive using the NB-IoT standard. Examples of devices using this standard include smart watches and smart-home devices.

The Wi-Fi module 108 uses a WiFi radio configured to transmit and receive using the IEEE 802.11 standard. In addition to communicating with laptop computers, tablet, mobile devices, and other devices, the Wi-Fi radio is configured to receive the wireless transmission from the medical device 14 or a base station (e.g., the monitor 16) in communication with the medical device 14.

The LoRa module 110 uses a radio configured to transmit and receive using the LoRA standard. The LoRa module enables wireless communication at longer ranges than other modules in the communication suite 46. Examples of devices using this standard include asset trackers and fire detection systems.

The LTE module 112 uses a radio configured to transmit and receive using the LTE standard and/or 5G standard or other suitable broadband cellular network standards. This module allows the connected device 10 to connect to a network of a mobile service provider (MSP), for example.

The ethernet module 114 includes at least one ethernet port through which the connected device 10 may connect to, for example, a modem, the intermediate network waypoint 36 as depicted in FIG. 1B, or any other device having an ethernet port.

As described above, the connected device 10 may connect to a modem, however the connected device 10 also includes an integrated modem 116. In one configuration the integrated modem 116 is a cable modem 116A configured to transmit and receive data via a coaxial cable, although in other configurations, the integrated modem 116 is an optical modem 116B, a dial-up modem 116C, a satellite modem 116D, a powerline modem 116E, or any other suitable type of modem.

Returning now to FIG. 2A, in order to isolate data flows, bridging functions are performed by a client bridge 92, a mesh/cluster bridge 94, and/or a WAN bridge 96. The interfaces of the communication suite 46 are attached on a policy basis to instances of a modular forwarding system 90.

The modular forwarding system 90 engages modules and executes configured operations. A description of the modules follows.

An autoconfiguration module 58 enables zero touch provisioning of the connected device 10 when the connected device 10 is first installed in the target environment such as the patient environment. The autoconfiguration module 58 accesses a configuration database of the global zero-touch provisioning system of the smart cloud 24. The configuration database includes configuration data for the patient including a device identification, a clinic identification, a patient identification, and/or a transmission schedule. The configuration data is entered into the configuration database before the patient first deploys the connected device 10. Upon a first bootup of the connected device 10 in the patient environment, the connected device 10 is configured to send a request to the global zero-touch provisioning system of the smart cloud 24 which uses the configuration data to configure the connected device 10 with no input from the patient 12.

A unified radio management module 60 selects channels and power controls for all radios and modules in the communication suite 46 on a policy basis. Additionally, the unified radio management module 60 determines whether data transmissions with the Internet 22 or other destinations occur via the LTE radio or via the broadband connection. For example, in a scenario in which the broadband connection is available, the unified radio management module 60 may direct the connected device 10 to transmit data via the broadband connection. As another example, in a scenario in which the broadband connection is unavailable, the unified radio management module 60 directs data to be transmitted via the LTE radio based on a data category of the data. Similarly, data originating from the medical device 14 and categorized as medical data may be transmitted via the LTE radio while other data (e.g., streaming video categorized as non-medical data) may be restricted until the broadband connection is restored. Such a configuration ensures that important medical data is transmitted while preventing excessive expenses from being incurred due to high levels of other data being transmitted via the LTE radio. Alternatively, the connected device 10 is configurable such that both medical data and non-medical data are transmitted by the LTE radio. It will be appreciated that while the above example categorized data into medical data and non-medical data, other data categories may be used. For example, data may be categorized as streaming video data, voice over internet protocol (VioP) data, or any other category based on content of the data. Additionally or alternatively, data may be categorized by a device from which the data originated (e.g., from the patient mobile device 18, from the medical device 14, from a laptop computer, or any other device 20).

In order to ensure that all medical data transmitted by the medical device 14 is appropriately forwarded even when network conditions are not ideal, the connected device 10 is configured to store medical data transmitted by the medical device. By storing the medical data as stored medical data in memory of the connected device 10, the medical device 14 may not repeatedly send a particular transmission more than once, which serves to extend the battery life of the medical device 14. The connected device 10 is configured to forward the medical data at a subsequent point in time. The subsequent point in time is determined in part by at least one of a user-selection of a time period, a determination that bandwidth used by the connected device 10 is below a predetermined threshold, and a determination that a previous data transmission failed. The user-selection of a time period allows the user to select a forwarding time at which forwarding of the medical data occurs. The user in this example may be the patient 12, a clinician, and/or other person having appropriate permissions to select the forwarding time. The user may also be a program implemented by a server. An advantage of this configuration is that the program can coordinate with multiple medical devices 14 and connected devices 10 deployed in different environments and request from each of the multiple connected devices 10 forwarding of the medical data in a coordinated fashion such that the server does not receive more medical data than can be processed at once. The determination that bandwidth used by the connected device is below a predetermined threshold allows the medical data to be forwarded when sufficient bandwidth is available for the connected device 10 to do so. The predetermined threshold may be determined by the user or by the connected device 10 and may be a percentage (e.g., 5%, 10%, 15%, 20%, or 25%) of total bandwidth or a specific bitrate. Because the connected device 10 is configured to determine that a previous transmission has failed, the previous transmission can be resent by the connected device 10 rather than by the medical device 14, thereby reducing the battery power expended by the medical device 14.

An authentication and security module 62 manages certificates and keys based on credentials provided or provisioned. The authentication and security module 62 assigns a device-level certificate to each device that is connected to the connected device 10. This module is also responsible for access controls when, for example, an EHR or EMR is accessed by the connected device or when a software or firmware update is sent to the medical device 14. In addition, the connected device 10 uses the authentication and security module 62 in conjunction with the processing agent 54 for other security functions. For example, the processing circuitry 44 of the connected device 10 is further configured to execute a firewall that controls permission to communicate via ports of the connected device 10, and the processing agent 54 is configured to identify a set of ports requested by the medical device 14 and instruct the firewall to allow access to the virtual machine, container, serverless instance or other environment in which the processing agent 54 is implemented only via those identified ports. In this way, an attack surface of the connected device 10 is minimized, and can help to secure the connected device 10 from hackers, malware, and/or other security threats.

In order to identify ports in the firewall used for medical data and restrict access of non-medical data to those ports, the processing agent 54 is configured to dynamically allocate ports on the firewall by identifying by machine learning during a learning phase in which the ports on the firewall are not locked down, a set of ports requested by the medical device 14. After identifying the set of ports, the processing agent 54 allows access to the virtual machine, container, or serverless instance executing the processing agent 54 via the identified set of ports, and locks a remainder of the ports.

The connected device 10 includes a location discovery module 64 that locates a position of the medical device 14 in relation to the connected device 10 and/or monitor 16. Where multiple connected devices 10 are available, the location discovery module 64 uses signal strength based multi-lateration approaches to track the medical device 14 and project distance to the monitor 16. Where multiple connected devices 10 are not present, other methods are used to locate the medical device 14. For example, remote signal strength probing and device-based simultaneous location and mapping (SLAM) methods may be incorporated using magnetic or inertial sensors. As described above, a substantial portion of missed transmissions for a medical device 14 can be attributed to patients 12 not being near their monitors 16 at preconfigured times. Information acquired in this module can be used to change behavior via new alerts, or can prompt changes to configurations at physical device follow-ups. Additionally, the location discovery module 64 can be used in part to determine that the wireless transmission originated from the medical device 14 by determining a distance between the connected device 10 and the medical device 14 using one or more of round-trip time and received signal strength, recording the distance between the connected device 10 and the medical device 14 over time as a distance log, and determining an identity of the medical device 14 based at least in part on the distance log.

A segmentation and tunnel module 68 supports an extensible tunnel encapsulation and decapsulation function that adapts to a variety of common encryption and tunneling protocols including internet protocol security (IPSec), generic routing encapsulation (GRE), general packet radio service (GPRS) tunneling protocol (GTP), secure socket layer (SSL) protocol, transport layer security (TLS) protocol, federal information processing publication standard (FIPS) 140-2, and/or other encryption and tunneling protocols. An overlay entity is engaged to protect low security devices from man in the middle (MiTM) attacks over the Internet. As discussed above, for a wireless transmission originating from the medical device 14, the connected device 10 performs medical device-specific processing on the wireless transmission. One example, performed in part with the segmentation and tunnel module 68, of performing medical device-specific processing on the wireless transmission includes encrypting the wireless transmission according to an encryption protocol and transmitting the encrypted wireless transmission to a destination server.

A CIED data management module 82 is responsible for secure edge acquisition of CIED events and alerts. Example CIED events or cardiac events include a myocardial infarction, an irregular heartbeat, a pulse rate above or below a predetermined threshold, or any condition that the CIED is able to detect. While this module is referred to as the CIED data management module 82 and the above examples are CIED events, it will be appreciated that the module is also configured for secure edge acquisition of events and alerts from the above-mentioned medical devices, or other medical devices. In an example scenario of event acquisition, the processing circuitry 44 is further configured to read an encoded cardiac signal from the wireless transmission, input the encoded cardiac signal into an artificial intelligence model 84 to thereby determine that a cardiac event has occurred, and upon determining that a cardiac event has occurred, transmit a notification of the cardiac event to a recipient address of a registered account. As an alternative to the artificial intelligence model 84, the encoded cardiac signal may also be inputted into a deterministic model to thereby determine that the cardiac event has occurred. The connected device 10 is configured to contact emergency medical services (e.g., 911 in the United States) upon determining that a cardiac event has occurred. A benefit of this configuration is that the connected device 10 alerts appropriate medical personnel even if the patient 12 is unable or unaware that a cardiac event has occurred. Other features of this module include protected health information (PHI) and personally identifiable information (PII) filtering controls with highly restricted internal system access.

The processing agent 54 may further comprise a flow/session management module 66, a deep visibility module 70, an application gateway module 72, a content filtering module 74, a WAN optimization module 76, an application assurance module 78, and/or a management telemetry module 80.

With reference now to FIGS. 3A-G, a flow diagram is illustrated depicting an example method 500 for communicating via a connected device. The following description of method 500 is provided with reference to the software and hardware components described herein and shown in FIGS. 1A-2B. For example, the method 500 may be performed by the connected device 10, hardware, software, and/or firmware of the connected device 10, or a suitable combination of components described herein.

It will be appreciated that the following description of method 500 is provided by way of example and is not meant to be limiting. Therefore, it is to be understood that method 500 may include additional and/or alternative steps relative to those illustrated in FIGS. 3A-G. Further, it is to be understood that the steps of method 500 may be performed in any suitable order. Further still, it is to be understood that one or more steps may be omitted from method 500 without departing from the scope of this disclosure. It will also be appreciated that method 500 also may be performed in other contexts using other suitable components.

Turning now to FIGS. 3A-G, the method 500 includes at 502, a set-up step. Details of the set-up step are described at a later section. At 504, the method 500 includes receiving a wireless transmission from a medical device. At 506, the method 500 includes receiving a wireless transmission via a radio, wherein the wireless transmission is in a Medical Device Radiocommunications Service spectrum. Additionally or alternatively to 506, the method 500 includes at 508 receiving the wireless transmission as a wireless transmission using a licensed, lightly licensed, or unlicensed frequency band from the medical device or from a base station in communication with the medical device. WiFi and Bluetooth are examples of a wireless technology that operates on wireless unlicensed frequency bands, and LTE is an example of a wireless technology operating on licensed or lightly licensed frequency bands.

At 510, the method 500 includes determining that a wireless transmission originated from the medical device. At 512, the method 500 includes inspecting the wireless transmission to identify a signal characteristic, header data, or payload data of the wireless transmission. At 514, the method 500 includes determining that the signal characteristic, header data, and/or payload data of the wireless transmission matches a predetermined medical device signal characteristic, header data, and/or payload data. At 516, the method 500 includes determining a distance between the connected device and the medical device using one or more of round-trip time and received signal strength. At 518, the method 500 includes recording the distance between the connected device and the medical device over time as a distance log. At 520, the method 500 includes determining an identity of the medical device based at least in part on the distance log. At 522, the method 500 includes upon determining that the wireless transmission originated from the medical device, performing medical device-specific processing on the wireless transmission.

At 524, the method 500 includes outputting processing results. At 525A, the method 500 includes transmitting processing results to a recipient device. At 525B, the method 500 includes storing and/or executing on a local device.

In the depicted example, at 526, the method 500 includes implementing a computing environment configured to execute a processing agent including a medical device detector configured to perform the inspecting of the wireless transmission to identify the signal characteristic, header data, or payload data of the wireless transmission; and the determining that the signal characteristic, header data, and/or payload data of the wireless transmission matches the predetermined medical device signal characteristic, header data, and/or payload data. In one example, the computing environment may be a virtualized machine environment including a hypervisor communicating with one or more virtual machines, each virtual machine including an operating system instance, and at least one of the virtual machines configured execute the processing agent. In other examples, the method 500 may include implementing a container environment including a container interface configured to communicate between software in one or more containers and an operating system executed by the processing circuitry. Each container does not include an operating system instance, and wherein at least one of the containers is configured to execute the processing agent. In yet other examples, the method 500 may include implementing a serverless environment including a plurality of functional software modules that present microservice instances that process individual functions for requesting clients, and wherein the server environment is configured to execute the processing agent. It will be appreciated that these are illustrative examples, and the processing agent may be implemented in other computing environments, such as in an operating system, embedded system, system-on-chip or other hardware (e.g., ASIC/FPGA) environment.

At 528, the method 500 includes executing a firewall that controls permission to communicate via ports of the connected device. At 530, the method 500 includes via the processing agent, identifying a set of ports requested by the medical device. At 532, the method 500 includes instructing the firewall to allow access to the virtual machine, container, serverless instance, or other computing environment in which the processing agent is implemented only via those identified ports. It will be appreciated that steps 526 and 528 are examples of sub-steps of set-up, 502.

At 534, the method 500 includes via the processing agent, dynamically allocating ports on the firewall. At 536, the method 500 includes identifying by machine learning during a learning phase in which the ports on the firewall are not locked down, a set of ports requested by the medical device. At 538, the method 500 includes after identifying the set of ports, allowing access to the virtual machine (VM), container, or serverless instance or other environment executing the processing agent via the identified set of ports and locking a remainder of the ports.

At 540, the method 500 includes reading an encoded patient health signal from the wireless transmission. At 542, the method 500 includes inputting the encoded patient health signal into an artificial intelligence model to thereby determine that an adverse health or device event has occurred. At 544, the method 500 includes upon determining that the adverse health or device event has occurred, transmitting a notification of the adverse health or device event to a recipient address of a registered account.

At 546, the method 500 includes storing medical data transmitted by the medical device. At 548, the method 500 includes forwarding the medical data at a subsequent point in time, the subsequent point in time being determined in part by at least one of a user-selection of a time period, a determination that bandwidth used by the connected device is below a predetermined threshold, and a determination that a previous data transmission failed.

At 550, the method 500 includes encrypting the wireless transmission according to an encryption protocol. At 552, the method 500 includes transmitting the encrypted wireless transmission to a destination server.

At 554, the method 500 includes prioritizing processing of data contained in the wireless transmission over processing of data contained in other wireless transmissions. At 556, the method 500 includes transmitting the prioritized data contained in the wireless transmission to a destination server.

At 558, the method 500 includes storing and performing local analytics for medical device event data and/or telemetry. At 560, the method 500 includes transmitting the stored data and local analytics data to a destination server.

In some embodiments, the methods and processes described herein may be tied to a computing system of one or more computing devices. In particular, such methods and processes may be implemented as a computer-application program or service, an API, a library, and/or other computer-program product.

Figure 4:
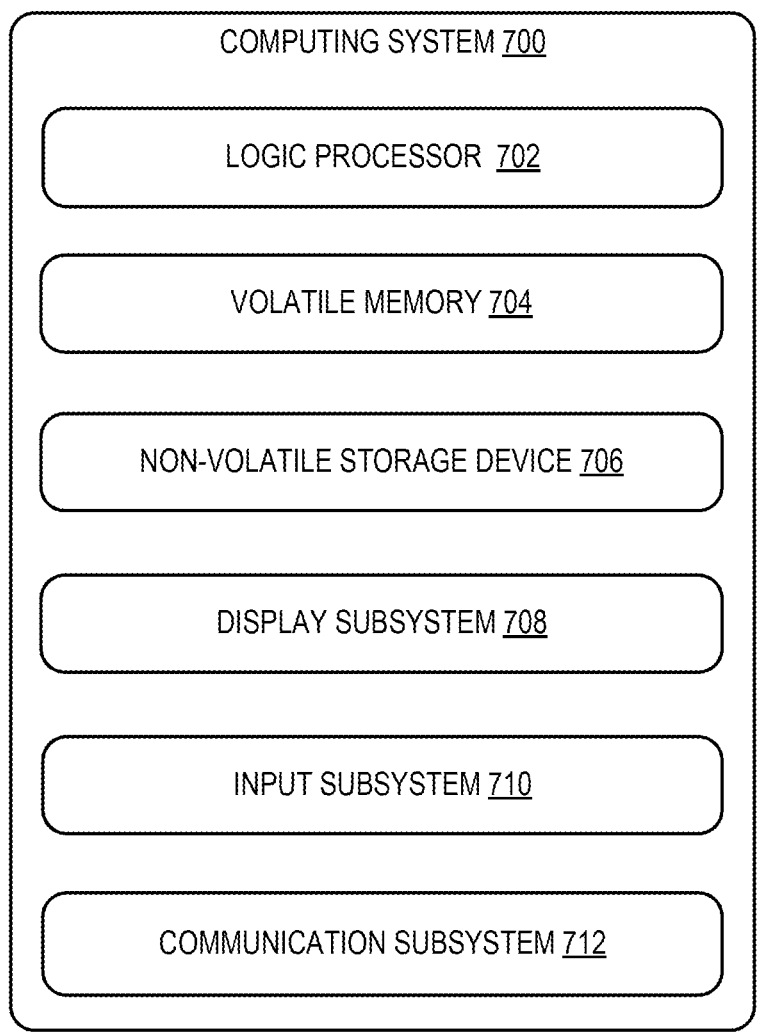
FIG. 4 is an example computing environment that may be used to implement the system of FIGS. 1A-C.

FIG. 4 schematically shows a non-limiting embodiment of a computing system 700 that can enact one or more of the methods and processes described above. Computing system 700 is shown in simplified form. Computing system 700 may embody the connected device 10 described above and illustrated in FIGS. 2A, B. Computing system 700 may take the form of one or more personal computers, server computers, tablet computers, home-entertainment computers, network computing devices, gaming devices, mobile computing devices, mobile communication devices (e.g., smart phone), and/or other computing devices, and wearable computing devices such as smart wristwatches and head mounted augmented reality devices.

Computing system 700 includes a logic processor 702 volatile memory 704, and a non-volatile storage device 706. Computing system 700 may optionally include a display subsystem 708, input subsystem 710, communication subsystem 712, and/or other components not shown in FIG. 4.

Logic processor 702 includes one or more physical devices configured to execute instructions. For example, the logic processor may be configured to execute instructions that are part of one or more applications, programs, routines, libraries, objects, components, data structures, or other logical constructs. Such instructions may be implemented to perform a task, implement a data type, transform the state of one or more components, achieve a technical effect, or otherwise arrive at a desired result.

The logic processor may include one or more physical processors (hardware) configured to execute software instructions. Additionally or alternatively, the logic processor may include one or more hardware logic circuits or firmware devices configured to execute hardware-implemented logic or firmware instructions. Processors of the logic processor 702 may be single-core or multi-core, and the instructions executed thereon may be configured for sequential, parallel, and/or distributed processing. Individual components of the logic processor optionally may be distributed among two or more separate devices, which may be remotely located and/or configured for coordinated processing. Aspects of the logic processor may be virtualized and executed by remotely accessible, networked computing devices configured in a cloud-computing configuration. In such a case, these virtualized aspects are run on different physical logic processors of various different machines, it will be understood.

Non-volatile storage device 706 includes one or more physical devices configured to hold instructions executable by the logic processors to implement the methods and processes described herein. When such methods and processes are implemented, the state of non-volatile storage device 706 may be transformed—e.g., to hold different data.

Non-volatile storage device 706 may include physical devices that are removable and/or built-in. Non-volatile storage device 706 may include optical memory (e.g., CD, DVD, HD-DVD, Blu-Ray Disc, etc.), semiconductor memory (e.g., ROM, EPROM, EEPROM, FLASH memory, etc.), and/or magnetic memory (e.g., hard-disk drive, floppy-disk drive, tape drive, MRAM, etc.), or other mass storage device technology. Non-volatile storage device 706 may include nonvolatile, dynamic, static, read/write, read-only, sequential-access, location-addressable, file-addressable, and/or content-addressable devices. It will be appreciated that non-volatile storage device 706 is configured to hold instructions even when power is cut to the non-volatile storage device 706.

Volatile memory 704 may include physical devices that include random access memory. Volatile memory 704 is typically utilized by logic processor 702 to temporarily store information during processing of software instructions. It will be appreciated that volatile memory 704 typically does not continue to store instructions when power is cut to the volatile memory 704.

Aspects of logic processor 702, volatile memory 704, and non-volatile storage device 706 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The terms "module," "program," and "engine" may be used to describe an aspect of computing system 700 typically implemented in software by a processor to perform a particular function using portions of volatile memory, which function involves transformative processing that specially configures the processor to perform the function. Thus, a module, program, or engine may be instantiated via logic processor 702 executing instructions held by non-volatile storage device 706, using portions of volatile memory 704. It will be understood that different modules, programs, and/or engines may be instantiated from the same application, service, code block, object, library, routine, API, function, etc. Likewise, the same module, program, and/or engine may be instantiated by different applications, services, code blocks, objects, routines, APIs, functions, etc. The terms "module," "program," and "engine" may encompass individual or groups of executable files, data files, libraries, drivers, scripts, database records, etc.

When included, display subsystem 708 may be used to present a visual representation of data held by non-volatile storage device 706. The visual representation may take the form of a graphical user interface (GUI). As the herein described methods and processes change the data held by the non-volatile storage device, and thus transform the state of the non-volatile storage device, the state of display subsystem 708 may likewise be transformed to visually represent changes in the underlying data. Display subsystem 708 may include one or more display devices utilizing virtually any type of technology. Such display devices may be combined with logic processor 702, volatile memory 704, and/or non-volatile storage device 706 in a shared enclosure, or such display devices may be peripheral display devices.

When included, input subsystem 710 may comprise or interface with one or more user-input devices such as a keyboard, mouse, touch screen, or game controller. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity; and/or any other suitable sensor.

When included, communication subsystem 712 may be configured to communicatively couple various computing devices described herein with each other, and with other devices. Communication subsystem 712 may include wired and/or wireless communication devices compatible with one or more different communication protocols. As non-limiting examples, the communication subsystem may be configured for communication via a wireless telephone network, or a wired or wireless local- or wide-area network, such as a HDMI over Wi-Fi connection. In some embodiments, the communication subsystem may allow computing system 700 to send and/or receive messages to and/or from other devices via a network such as the Internet.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A connected device, comprising:
   a communications suite including at least one module selected from the group consisting of a Zigbee module, a Bluetooth Low Energy (BLE) module, a narrow-band internet of things (NB-IoT) module, a Wi-Fi module, a LoRa module, and a long-term evolution (LTE) module; and
   processing circuitry configured to:
      implement a computing environment selected from a group consisting of a virtual machine environment, a container environment, and a serverless environment;
      receive a wireless transmission from an implantable medical device via the at least one module of the communications suite;
      determine that the wireless transmission originated from the implantable medical device by executing, in the computing environment, a processing agent including a medical device detector configured to perform:
         inspecting the wireless transmission to identify a signal characteristic, header data, or payload data of the wireless transmission;
         determining that the signal characteristic, header data, and/or payload data of the wireless transmission matches a predetermined medical device signal characteristic, header data, and/or payload data; and upon determining that the wireless transmission originated from the implantable medical device, perform medical device-specific processing on the wireless transmission, wherein determining that the wireless transmission originated from the implantable medical device includes:

determining a distance between the connected device and the implantable medical device using one or more of round-trip time and received signal strength;

recording the distance between the connected device and the implantable medical device over time as a distance log; and determining an identity of the implantable medical device based at least in part on the distance log.

2. The connected device of claim 1, wherein performing medical device-specific processing includes prioritizing processing of data contained in the wireless transmission over processing of data contained in other wireless transmissions.

3. The connected device of claim 1, further comprising a radio transceiver configured to transmit and receive on a licensed, lightly licensed, or unlicensed radio frequency band, and wherein the wireless transmission is received via the radio transceiver.

4. The connected device of claim 1, wherein the module is the Wi-Fi module, the connected device further comprising:

a Wi-Fi radio configured to receive the wireless transmission from the implantable medical device or a base station in communication with the implantable medical device.

5. The connected device of claim 1, wherein the module is the Bluetooth Low Energy (BLE) module, the connected device further comprising:

a Bluetooth Low Energy (BLE) radio configured to receive the wireless transmission from the implantable medical device or a base station in communication with the implantable medical device.

6. The connected device of claim 1, wherein the processing circuitry is further configured to execute a firewall that controls permission to communicate via ports of the connected device; and the processing agent is configured to identify a set of ports requested by the implantable medical device and instruct the firewall to allow access to the computing environment in which the processing agent is implemented only via those identified ports.

7. The connected device of claim 6, wherein the processing agent is configured to dynamically allocate ports on the firewall by:

identifying by machine learning during a learning phase in which the ports on the firewall are not locked down, a set of ports requested by the implantable medical device; and after identifying the set of ports, allowing access to the computing environment executing the processing agent via the set of ports identified and locking a remainder of the ports.

8. The connected device of claim 1, wherein the processing circuitry is further configured to:

read an encoded health signal from the wireless transmission;

input the encoded health signal into an artificial intelligence model to thereby determine that a health event has occurred; and upon determining that an adverse health or device event has occurred, transmit a notification of the adverse health or device event to a recipient address of a registered account.

9. The connected device of claim 1, wherein the processing circuitry is further configured to:

store medical data transmitted by the implantable medical device and forward the medical data at a subsequent point in time, the subsequent point in time being determined in part by at least one of the following:

a user-selection of a time period;

a determination that bandwidth used by the connected device is below a predetermined threshold, and a determination that a previous data transmission failed.

10. The connected device of claim 1, wherein performing medical device-specific processing on the wireless transmission includes:

encrypting the wireless transmission according to an encryption protocol; and transmitting the encrypted wireless transmission to a destination server.

11. A method for communicating via a connected device, comprising:

receiving a wireless transmission from an implantable medical device via a module of a communications suite of the connected device, the module being selected from the group consisting of a Zigbee module, a Bluetooth Low Energy (BLE) module, a narrow-band internet of things (NB-IoT) module, a Wi-Fi module, a LoRa module, and a long-term evolution (LTE) module;

determining that the wireless transmission originated from the implantable medical device by:

inspecting the wireless transmission to identify a signal characteristic, header data, or payload data of the wireless transmission;

determining that the signal characteristic, header data, and/or payload data of the wireless transmission matches a predetermined medical device signal characteristic, header data, and/or payload data;

determining a distance between the connected device and the implantable medical device using one or more of round-trip time and received signal strength;

recording the distance between the connected device and the implantable medical device over time as a distance log;

determining an identity of the implantable medical device based at least in part on the distance log; and upon determining that the wireless transmission originated from the implantable medical device, performing medical device-specific processing on the wireless transmission.

12. The method of claim 11, wherein the module is the Wi-Fi module, the method further comprising:

receiving the wireless transmission as a WiFi transmission from the implantable medical device or from a base station in communication with the implantable medical device.

13. The method of claim 11, wherein the module is the Bluetooth Low Energy (BLE) module, the method further comprising:

receiving the wireless transmission as a Bluetooth Low Energy (BLE) transmission from the implantable medical device or from a base station in communication with the implantable medical device.

14. The method of claim 11, further comprising:
implementing a computing environment selected from a group consisting of a virtual machine environment, a container environment, and a serverless environment, wherein
the computing environment is configured to execute a processing agent including a medical device detector configured to perform:
the inspecting of the wireless transmission to identify the signal characteristic, header data, or payload data of the wireless transmission; and
the determining that the signal characteristic, header data, and/or payload data of the wireless transmission matches the predetermined medical device signal characteristic, header data, and/or payload data.

15. The method of claim 14, further comprising:
executing a firewall that controls permission to communicate via ports of the connected device; and
via the processing agent:
identifying a set of ports requested by the implantable medical device; and
instructing the firewall to allow access to the computing environment in which the processing agent is implemented only via those identified ports.

16. The method of claim 15, further comprising, via the processing agent:
dynamically allocating ports on the firewall by:
identifying by machine learning during a learning phase in which the ports on the firewall are not locked down, a set of ports requested by the implantable medical device; and
after identifying the set of ports, allowing access to the computing environment executing the processing agent via the set of ports identified and locking a remainder of the ports.

17. The method of claim 11, further comprising:
reading an encoded health signal from the wireless transmission;
inputting the encoded health signal into an artificial intelligence model to thereby determine that a health event has occurred; and
upon determining that an adverse health or device event has occurred, transmitting a notification of the adverse health or device event to a recipient address of a registered account.

18. The method of claim 11, further comprising:
storing medical data transmitted by the implantable medical device and forwarding the medical data at a subsequent point in time, the subsequent point in time being determined in part by at least one of the following:
a user-selection of a time period;
a determination that bandwidth used by the connected device is below a predetermined threshold, and
a determination that a previous data transmission failed.

19. The method of claim 11, wherein performing medical device-specific processing on the wireless transmission includes:
encrypting the wireless transmission according to an encryption protocol; and
transmitting the encrypted wireless transmission to a destination server.

* * * * *